United States Patent [19]

Griffith et al.

[11] Patent Number: 5,472,968
[45] Date of Patent: Dec. 5, 1995

[54] SPIRO[CYCLOALKYLBENZENE-1,1'-(1',2',3',4'-TETRAHYDRO-ISOQUINOLINES)] HAVING NEUROPROTECTIVE PROPERTIES

[75] Inventors: Ronald C. Griffith, Pittsford; James R. Matz, Fairport, both of N.Y.; James J. Napier, Lindenhurst, Ill.

[73] Assignee: Fisons Corporation, Rochester, N.Y.

[21] Appl. No.: 975,932

[22] PCT Filed: Aug. 19, 1991

[86] PCT No.: PCT/US91/05887

§ 371 Date: Mar. 16, 1993

§ 102(e) Date: Mar. 16, 1993

[87] PCT Pub. No.: WO92/03420

PCT Pub. Date: Mar. 5, 1992

Related U.S. Application Data

[63] Continuation of Ser. No. 573,574, Aug. 24, 1990, abandoned.

[51] Int. Cl.⁶ .................... A61K 31/47; C07D 217/04
[52] U.S. Cl. ................................ 514/278; 546/18
[58] Field of Search ................ 546/18; 514/278

[56] References Cited

U.S. PATENT DOCUMENTS 3,886,163  5/1975  Kadin ....................... 260/281

OTHER PUBLICATIONS

Grelan, Chemical Abstract vol. 74, No. 141571b (1971).
Kametani et al, J. Chem. Soc. (c), (1971), pp. 1032–1043.

Primary Examiner—Philip I. Datlow
Attorney, Agent, or Firm—McAulay Fisher Nissen Goldberg & Kiel

[57] ABSTRACT

Compounds of formula (I),

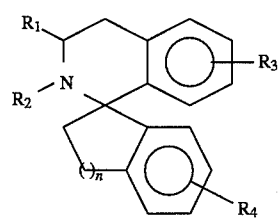

in which $R_1$ and $R_2$, which may be the same or different, represent hydrogen, $C_{1-6}$ alkyl, $R_3$ and $R_4$ independently represent one or more radicals selected from hydrogen, OH, $NH_2$, $NO_2$, halogen, $C_{1-6}$ alkyl or $C_{1-6}$ alkoxy and n is an integer from 1–2 inclusive, and pharmaceutically acceptable derivatives thereof are useful as pharmaceuticals; in particular, they possess N-methyl-(d)-aspartate(NMDA) blocking properties and are useful in the treatment and/or prevention of neurodegenerative conditions.

9 Claims, No Drawings

SPIRO[CYCLOALKYLBENZENE-1,1'-(1',2',3',4'-TETRAHYDRO-ISOQUINOLINES)] HAVING NEUROPROTECTIVE PROPERTIES

This is a continuation of application Ser. No. 07/573,574, filed Aug. 24, 1990, now abandoned.

This invention relates to novel spiro[cycloalkylbenzene-1,1'-(1',2',3',4'-tetrahydroisoquinolines)], processes for their preparation, pharmaceutical formulations containing them and their neuroprotective properties.

BACKGROUND

Compounds which possess N-methyl-(d)-aspartate (NMDA) blocking properties are useful in the treatment and/or prevention of neurodegeneration in pathological conditions such as stroke, cerebral ischaemia, cerebral palsy, hypoglycaemia, epilepsy, Alzheimer's disease, Huntington's chorea, Olivo-ponto-cerebellar atrophy, perinatal asphyxia and anoxia.

Kametani et al. [J. Chem. Soc.(C) 112–118 (1968) investigated isoquinoline alkaloid derivatives and obtained 1',2',3',4'-tetrahydro-6'-hydroxy-5,6,7'-trimethoxyspiro[indane-1,1'-isoquinoline] as a product of phenolic cyclization.

Spiro[indane-1,1'-isoindoline] was disclosed by Robinson et al[Tet. Letts. 30. 5203–5206 (1989)]. No biological data were reported.

DETAILED DESCRIPTION

According to the invention, we provide compounds of the formula I:

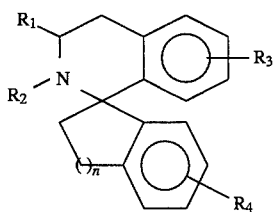

wherein $R_1$ and $R_2$, independently represent H or $C_{1-6}$ alkyl;

$R_3$ and $R_4$ independently represent one to four radicals selected from H, OH, $NH_2$, $NO_2$, halogen, $C_{1-6}$ alkyl or $C_{1-6}$ alkoxy;

n is 1 or 2, in addition, the spiro rings may independently contain an unsaturated carbon-carbon bond;

and pharmaceutically acceptable derivatives thereof;
provided that when n is 1; $R_1$ is H; and (a) $R_2$ represents methyl and $R_3$ represents 6',7'-dimethoxy; then $R_4$ is other than 5,6,7-trimethoxy;

(b) $R_2$ represents methyl and $R_3$ represents 6'-methoxy, 7'-OH; then $R_4$ is other than 5,6,7 -trimethoxy;

(c) $R_2$ represents H and $R_3$ represents 6'-OH,7'-methoxy; then $R_4$ is other than 4,5-dimethoxy;

(d) $R_2$ represents H and $R_3$ represents 6'-OH,7'-methoxy; then $R_4$ is other than 5,6-dimethoxy.

Pharmaceutically acceptable derivatives include pharmaceutically acceptable acid addition salts and compounds which will be suitable bioprecursors (prodrugs) of the compound of formula I.

Pharmaceutically acceptable acid addition salts of the compounds of formula I include salts of mineral acids, for example, hydrohalic acids, eg hydrochloric or hydrobromic; or organic acids, for example, formic, acetic or lactic acids. The acid may be polybasic, for example sulphuric, fumaric, maleic or citric acid.

Suitable bioprecursors of the compounds of formula I include $C_{1-6}$ alkanoyl amides, urethane derivatives and amino acid amide derivatives of one or more of the amino groups, and when a compound of formula I bears a hydroxyl group, esters of alkanoic and amino acids. Urethane derivatives include $C_{1-6}$ alkoxycarbonyl groups. Amino acid amide and ester derivatives may be formed from alpha-amino acids.

Alpha-amino acids may be represented by the formula II:

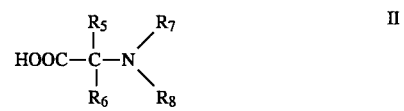

in which, $R_5$ represents hydrogen, $C_{1-6}$alkyl, hydroxy- $C_{1-2}$ alkyl, mercaptomethyl, (methylthio)$C_{1-2}$alkyl, carboxy-$C_{1-2}$alkyl, 2-($C_{1-3}$alkoxy)ethyl, (aminocarbonyl)$C_{1-2}$alkyl, amino-$C_{1-4}$alkyl, 3-imidazolylmethyl, phenylmethyl or (4-hydroxyphenyl)methyl, or in addition, $R_5$ together with the adjacent nitrogen may represent a piperidine, pyrrolidine or a 2-pyrrolidinone ring; and $R_6$, $R_7$ and $R_8$ independently represent hydrogen or $C_{1-6}$ alkyl, or in addition, $R_7$ and $R_8$ taken together with the nitrogen to which they are attached may represent a $C_{4-5}N$ heterocyclic ring;

Certain compounds of formula I and II may exist in different stereoisomeric forms, including optical enantiomeric forms. All are included within the scope of the invention.

According to another aspect of the invention, there is provided a process for the preparation of the compounds of formula I or pharmaceutically acceptable derivatives thereof, which comprises:

(a) preparing a compound of formula I in which $R_2$ is hydrogen by cyclizing the corresponding compound of formula III:

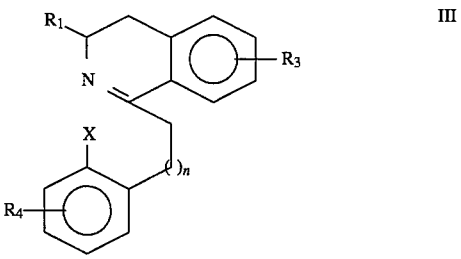

in which $R_1$, $R_3$, $R_4$ and n are as defined above, and X is a suitable leaving group, or (b) preparing a compound of formula I in which $R_2$ is $C_{1-6}$ alkyl by reacting the corresponding compound of formula I in which $R_2$ is hydrogen with an alkylating agent of the formula, $C_{1-6}$ alkyl-Y in which Y is a suitable leaving group, or (c) preparing a compound of formula I in which $R_2$ is $C_{1-6}$ alkyl by reducing the corresponding compound of formula I in which $R_2$ represents a $C_{1-6}$ alkanoyl group or a urethane group, or (d) preparing a compound of formula I in which $R_2$ is methyl by reacting the corresponding compound of formula I in which $R_2$ represents hydrogen with formaldehyde and formic acid, or (e) preparing a compound of formula I with an additional double bond in either or both of the spiro rings by halogenation-dehydrohalogenation of the corresponding compound of formula I, or (f) preparing a compound of formula I containing an amino or hydroxy group by removing a protecting group from a compound of formula I in which one or more of the amino or hydroxy groups is protected, and where desired or necessary, converting the corresponding compound of formula I to a pharmaceutically acceptable derivative thereof or vice-versa.

The cyclization reaction of process (a) may be carried out in the presence of a base, for example, butyl lithium in an aprotic solvent, for example, tetrahydrofuran and at a temperature of, for example, from −70°–80° C.

The alkylation reaction of process (b) may be carried out with an alkylating reagent, for example, iodomethane, bromoethane or methyl p-toluenesulfonate, in the presence of a base, for example, sodium hydroxide or pyridine in a suitable solvent, for example, water, ethanol or tetrahydrofuran or mixtures of the solvents, and at a temperature of, for example, from 0°–100° C.

The reduction reaction of process (c) may be carried out with a hydride reducing agent, for example, diborane or sodium bis(2-methoxyethoxy)aluminum hydride in an aprotic solvent, for example, tetrahydrofuran. The reduction may be carried out at a temperature of, for example, from 0°–100° C.

In the reaction of process (d) methylation is accomplished by heating the amine with formic acid and formaldehyde at a temperature of, for example, from 50°–100° C.

In the reaction of process (e) halogenation may be carried out with a suitable halogenating agent, for example, bromine, N-bromosuccinimide or sulfuryl chloride in a suitable inert solvent, for example, carbon tetrachloride or benzene and at a temperature of, for example, from 0°–150° C. Free radical initiators may be used, for example, benzoyl peroxide or light, to promote the reaction; dehydrohalogenation reactions may be carried out using conventional techniques, for example in the presence of a base, for example, potassium hydroxide in a protic solvent, for example ethanol, or in pyridine at temperatures of, for example, from 0°–120° C.

In the reaction of process (f), removal of the protecting group depends on the nature of the protecting group and includes acidic or basic cleavage or hydrogenolysis. Suitable amine protecting groups are, for example, ethoxycarbonyl, benzyloxycarbonyl, t-butyloxycarbonyl or $C_{1-3}$ alkanoyl. Protecting groups and methods for their removal are described in T. W. Greene, Protective Groups in Organic Syntheses, Wiley Interscience, 1981.

The starting materials for the products of reaction (a) can be made by a variety of methods, for example, the corresponding derivative of formula III may be prepared by cyclizing a compound of formula IV,

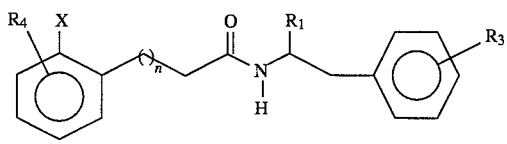

IV in which $R_1$, $R_3$, $R_4$ and n are as defined above and X is a suitable leaving group, preferably iodine, in the presence of a dehydrating agent, for example, phosphorous pentoxide in a suitable inert solvent, for example, xylene or toluene, and at a temperature of, for example, from 80°–140° C.

Compounds of the formula IV are either well known or may be prepared from compounds known per se by conventional methods or by modifications thereof as described in the examples.

The starting materials for the products of reaction (c) can be prepared by reacting the compound of formula I in which $R_2$ is hydrogen with a $C_{1-6}$ alkanoic acid anhydride, $C_{1-6}$ alkanoyl halide, $C_{1-6}$ haloformate ester, or an amino acid or a carboxyl activated derivative thereof, for example, acetic anhydride, acetyl chloride or ethyl chloroformate. The reactions may be carried out in the presence of a base, for example, sodium hydroxide or pyridine. The reactions may be carried out in the absence of a solvent; however, a suitable inert solvent may be used, for example, toluene, methylene chloride or tetrahydrofuran. The reactions may be carried out at a temperature of, for example, from 0°–100° C.

Pharmaceutically acceptable salts may be formed by reacting the free base, or a salt or derivative thereof with one or more equivalents of the appropriate acid. The reaction may be carried out in a solvent in which the salt is insoluble or in which the salt is soluble or in mixtures of the solvents. Acid addition salts may be converted to the corresponding base, for example, by reacting the salt with sodium hydroxide in water at room temperature.

Suitable bioprecursor forms of a compound of the formula I may be prepared by reacting the corresponding compound of formula I in which one or more of the amino or hydroxyl groups is unprotected with a $C_{1-6}$ alkanoic acid anhydride, $C_{1-6}$ alkanoyl halide, $C_{1-6}$ haloformate ester, or an amino acid or a carboxyl activated derivative thereof. Conventional acylation techniques for amines may be used. The reactions may be carried out in the presence of a base, for example, sodium hydroxide or pyridine. The reactions may be carried out in the absence of a solvent; however, a suitable inert solvent may be used, for example, toluene, methylene chloride or tetrahydrofuran. The reactions may be carried out at a temperature of, for example, from 0°–100° C. The condensation with alpha-amino acid derivatives may be carried out in conditions similar to those used for the synthesis of peptide bonds in protein chemistry, e.g. by carrying out the reaction in the presence of N,N'-carbonyldiimidazole in a polar aprotic solvent or using a hindered base, e.g. triethylamine and an alkyl chloroformate. When one or both of the amino acid nitrogen substituents is hydrogen, the nitrogen atom requires protection. One particularly suitable protecting group is benzyloxycarbonyl, which may readily be removed by hydrogenolysis or hydrogen bromide in acetic acid. Other groups that may be mentioned include t-butyloxycarbonyl (Boc), which is removed by standing the peptide in cold trifluoroacetic acid; Fmoc, which may be removed by treatment with dilute piperidine (20% in DMF); (4-methoxybenzyl)oxycarbonyl and 2-nitrophenylsulphenyl. Further protecting groups and methods for their removal are described in T. W. Greene, Protective Groups in Organic Synthesis, Wiley Interscience, 1981.

Resolution of compounds with asymmetric centers may be accomplished by methods well known in the art, for example, by separation of their diastereoisomeric salts, chromatography on a chiral column or asymmetric syntheses. Methods of resolution are described in J. March, Advanced Organic Chemistry, 3rd. Edition, Wiley Interscience, 1985.

In the compound of formula I, alkyl groups which $R_1$, $R_2$, $R_3$ and $R_4$ may represent include methyl, ethyl, propyl, isopropyl, n-butyl, isobutyl and s-butyl;

alkoxy groups which $R_3$ and $R_4$ may represent include methoxy, ethoxy and propoxy;

halogen groups which $R_3$ and $R_4$ may represent include fluorine, chlorine, bromine or iodine;

We prefer compounds of formula I or a pharmaceutically acceptable derivative thereof, in which:

$R_1$ and $R_2$ are independently selected from hydrogen, methyl or ethyl, especially hydrogen or methyl;

$R_3$ and $R_4$ are independently selected from hydrogen, hydroxy, amino or chloro.

We especially prefer compounds in which $R_3$ and $R_4$ are hydrogen.

A subgroup of compounds which are preferred are those in which, $R_1$ is hydrogen or methyl, and $R_2$ is hydrogen.

We especially prefer compounds in which n is 1.

Suitable bioprecursor groups which may be mentioned include acetyl, propionyl, butanoyl, methoxycarbonyl, ethoxycarbonyl and alpha-amino acids, for example, glycine, alanine, leucine, proline, methionine, serine and sarcosine. Derivatives of alpha-amino acids are preferred, especially glycine.

Certain compounds of formula I and their pharmaceutically acceptable derivatives are useful because they possess pharmacological activity in animals.

According to another aspect of the invention, there is provided the use of a compound of formula I as defined above, but without proviso (c,) and pharmaceutically acceptable derivatives thereof, as a pharmaceutical.

According to yet another aspect of the invention, there is provided the use of a compound of formula I, as defined above, but without provisos (a) to (d), and pharmaceutically acceptable derivatives thereof, in the manufacture of a medicament for use as a neuroprotective agent.

According to yet another aspect of the invention, there is provided a method of treatment of neurodegenerative conditions which comprises administering to a patient a therapeutically effective amount of a compound of formula I, as defined above, but without provisos (a) to (d), and pharmaceutically acceptable derivatives thereof.

The compounds have useful neuroprotective properties. In particular, they possess NMDA blocking properties. Neurodegeneration is known to be caused or accelerated by certain excitatory amino acids found naturally in the central nervous system (CNS). Glutamate is an endogenous amino acid which has been characterized as a fast excitatory transmitter in the mammalian brain. Glutamate is also known as a powerful neurotoxin capable of killing CNS neurons under certain pathologic conditions which accompany stroke and cardiac arrest. It has been shown that the sensitivity of central neurons to hypoxia and ischemia can be reduced by the specific antagonism of post synaptic glutamate receptors. Glutamate is characterized as a broad spectrum agonist having activity at four neuronal excitatory amino acid receptor sites. These receptor sites are named after the amino acids which selectively excite them: kainate (KA), N-methyl-D-aspartate (NMDA), quisqualate (QUIS) and 2-amino-4-phosphonobutyrate (APB). Glutamate is believed to be a mixed agonist capable of binding to and exciting all three receptor types. Thus, agents which selectively block or antagonise the action of glutamate at these receptors can prevent neurotoxic injury associated with anoxia, hypoxia or ischemia. In particular, compounds which bind to the NMDA receptor site and selectively block the action of glutamate are useful in the prevention and treatment of neurodegenerative diseases.

In addition, certain compounds of formula I demonstrate anticonvulsant activity by their ability to inhibit maximal electroshock (MES) induced seizures in mice; certain compounds inhibit the onset of convulsions and death induced by administration of nmda to mice; and certain compounds demonstrate antihypoxia activity by their ability to increase the survival time of mice in an oxygen depleted environment.

Antiepileptic activity may be measured by assessing a compound's ability to present the hind limb tonic extension component of the seizure in groups of mice induced by maximal electroshock (MES) after oral or intraperitoneal administration, according to the procedures of the Epilepsy Branch, NINCDS as published by R. J. Porter, et al., *Cleve. Clin. Quarterly* 1984, 51, 293, and compared to the standard agents dilantin and phenobarbital. Activities ($ED_{50}$'s) in the range of 10–400 m/k after oral administration in this assay system were obtained.

Certain compounds of this invention may possess useful antihypoxia activity. This activity may be conveniently measured in mice. Groups of mice are tested at various times after the intraperitoneal administration of graded doses of the test compound. The animals' survival time in a temperature-controlled hypoxic environment (96% nitrogen and 4% oxygen) is recorded. A statistical comparison is made between coincident vehicle treated animals and the experimental group. The dose-response and minimum active dose (MAD) for compounds are obtained. Other modes of administration can also be used.

NMDA activity may be measured in several ways:

a) NMDA blocking activity is measured by assessing a compound's ability to protect mice from convulsions induced by intravenous administration of 150 m/k of NMDA according to the procedures of Czuczwar et al., (Neurotransmitters, Seizures and Epilepsy III, edited by G. Nistico et al., Raven Press, New York 1986, pages 235–246). Groups of mice are pretreated by 30 min with the test compound by the oral or intraperitoneal routes and then given NMDA. Animals were observed for convulsions as defined by loss of righting reflex and appearance of tonic/clonic seizures. Animals are kept for 60 min after NMDA dosing and mortality was recorded.

b) NMDA receptor antagonist activity is measured in vitro by assaying a compounds ability to inhibit binding of the receptor antagonist 10,11-dihydro-5-methyl-5H-dibenzo[a,d]-cyclohepten-5,10-imine(MK801) to the receptor. The method is described by Foster and Wong, Br. J. Pharmacol. 91, 403–409 (1987). Briefly, crude brain membrane is prepared by homogenizing rat brain cortex and hippocampus in ice cold 0.32M sucrose. The homegenate is centrifuged and the resulting pellet is lysed by resuspending in ice cold distilled water. The membrane is collected by centrifugation and frozen at −70° C. for at least 18 hours. On the day of assay the membrane pellet is thawed and resuspended in 5 mM Tris-acetate at room temperature. The suspension is allowed to incubate at room temperature for 20 mins. and then collected by centrifugation. This process of suspension, incubation and centrifugation is repeated four times. The assay is carried out at room temperature for 45 mins. in a total volume of 1 mL containing 5 mM Tris-acetate, 2 nM [$^3$H]MK801 and test compound and 0.5 mL of membrane suspension under four conditions: a) added buffer, b) added 1 μM glycine, c) added 1 μM glutamate, and d) added 10 μM of both. The nonspecific binding is determined in the presence of 100 μM cold MK801. The reaction is terminated by rapid filtration through Whatman GF/B filter. The specific MK801 binding is defined as the total binding minus the binding in presence of 100 μM cold MK801.

Under these conditions, antagonists acting at the glycine site inhibit [$^3$H]MK801 binding alone or in the presence of glutamate, are partially reversed by 1 μM glycine (an agonist), and completely reversed by the high concentration of a glutamate and glycine mixture. Competitive glutamate antagonists inhibit [$^3$H]MK801 binding alone or in the presence of added glycine, are partially reversed by added glutamate (an agonist), and completely reversed by high concentrations of glutamate and glycine. Noncompetitive antagonists, which interact at the MK801 site inhibit [$^3$H]MK801 binding under all conditions.

c) NMDA and glycine receptor affinity may also be tested in the [$^3$H]L-glutamate and [$^3$H]glycine binding assays following the method of Monaghan & Cotman, PNAS, 83, 7532, (1986) and Watson et al, Neurosci. Res. Comm., 2, 169, (1988).

For the above-mentioned uses the dosage administered will, of course, vary with the compound employed, the mode of administration and the treatment desired. However, in general, satisfactory results are obtained when the compounds are administered at a daily dosage of from about 0.1 mg to about 20 mg per kg of animal body weight, preferably given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carrier or diluent.

The compounds of formula I, and pharmaceutically acceptable derivatives thereof, may be used on their own or in the form of appropriate medicinal preparations for enteral or parenteral administration.

According to the invention, there is also provided a pharmaceutical composition comprising preferably less than 80% and more preferably less than 50% by weight of a compound of formula I, or a pharmaceutically acceptable salt thereof, in admixture with a pharmaceutically acceptable adjuvant, diluent or carrier.

Examples of such adjuvants, diluents and carriers are: for tablets and dragees: lactose, starch, talc, stearic acid; for capsules: tartaric acid or lactose; for injectable solutions: water, alcohols, glycerin, vegetable oils; for suppositories: natural or hardened oils or waxes.

Compositions in a form suitable for oral, i.e. oesophageal administration include tablets, capsules and dragees;

Sustained release compositions include those in which the active ingredient is bound to an ion exchange resin which is optionally coated with a diffusion barrier to modify the release properties of the resin.

We prefer the composition to contain up to 50% and more preferably up to 25% by weight of the compound of formula I, or of the pharmaceutically acceptable derivative thereof.

The compounds of formula I and pharmaceutically acceptable derivatives thereof have the advantage that they are less toxic, more efficacious, are longer acting, have a broader range of activity, are more potent, produce fewer side effects, are more easily absorbed or have other useful pharmacological properties, than compounds of similar structure.

The invention is illustrated, but in no way limited, by the following examples:

EXAMPLE 1

Preparation of spiro[indane-1,1'-(1',2',3',4'-tetrahydroisoquinoline)] maleate a) N-(2-Phenylethyl)-2-iodobenzenepropionamide To a solution of 2-iodobenzenepropionic acid (8 g, 0.029 mol) and phenethylamine (10.9 g, 0.090 mol) in methylene chloride (200 mL) was added N-ethyl-N-[3-(dimethylamino)propyl]carbodiimide hydrochloride (6.13 g, 0.032 mol) at room temperature. After 3 days, water (100 mL) and 2.5N HCl (50 mL) were added. The organic phase was separated, dried and concentrated to give an oil (13.3 g). The oil was chromatographed on silica gel and eluted with hexane: ethyl acetate (2:1) then hexane: ethyl acetate (1:1) to give a fraction containing a yellow solid 7.6 g (69%). Recrystallization from toluene (15 mL) and petroleum ether (150 mL) afforded 7.1 g of product, mp. 94.5°–95.5° C.

b) 1-[2-(2-Iodophenyl)ethyl]-3,4-dihydroisoquinoline

To a suspension of phosphorous pentoxide (21.4 g, 0.15 mol) in xylene (150 mL) at reflux was added, portionwise, the amide from step (a) (7.1 g) dissolved in hot xylene (40 mL), during 30 minutes. The solution was then heated at reflux overnight, cooled to room temperature and diluted with 2.5N HCl (150 mL). The mixture was stirred for 2 hours, then water (200 mL) was added. The xylene layer was separated and the aqueous layer was basified with aqueous NaOH. The precipitate was extracted into diethyl ether and the ether layer was dried (MgSO$_4$), then concentrated to give the isoquinoline product as a solid, 5.9 g (87%), mp. 64.5°–66° C.

c) Spiro[indane-1,1'-(1',2',3',4'-tetrahydroisoquinoline)] maleate.

The iodide from step (b) (0.61 g, 1.7 mmol) in THF (5 mL) was added to a 1.7M solution of butyllithium (2.1 mmol) in THF (10 mL). After several hours, the reaction was quenched by the addition of water (1 mL). The reaction mixture was partitioned between ether and water and the ether layer was separated, dried (MgSO$_4$) and concentrated to give a yellow oil (0.41 g). Purification by chromatography on silica gel and elution with ammoniated chloroform gave the desired product, 0.34 g (80%) as a solid.

To a solution of the base (1.79 g, 7.39 mmol) in hot isopropanol (25 mL) was added maleic acid (0.87 g, 7.5 mmol). The solution was cooled to 0° C. and the precipitated salt was filtered (1.94 g). The solid was recrystallized from isopropanol to give the maleate salt of the title compound (1.33 g), mp 178°–178.5° C.

EXAMPLE 2

Preparation of spiro[indane-1,1'-(1',2',3',4'-tetrahydro-3'-methylisoquinoline)] maleate By following essentially the same procedures as described for example 1, steps a-c, and substituting α-methylphenethylamine for phenethylamine in step (a), spiro[indane-1,1'-(1',2',3',4'-tetrahydro-3'-methylisoquinoline)] was obtained as a mixture of steroisomers in the form of an oil. A sample of the oil (1.71 g) was chromatographed on silica gel and eluted with ammoniated ethyl acetate: hexane (1:10 and 1:5) to give a major isomer (0.98 g) and a minor isomer (0.13 g). The major isomer (0.98 g) was dissolved in isopropanol (8 ml) and maleic acid (0.47 g) was added. The maleate salt of the major isomer of the title product was thus obtained, wt=1.20 g, mp. 220°–220.5° C.

From NOE studies, the major isomer was identified as the trans isomer.

EXAMPLE 3

Preparation of Spiro[indane-1,1'-(1',2',3',4'-tetrahydro-2'-methylisoquinoline)]hydrobromide Spiro[indane-1,1'-(1',2',3',4'-tetrahydroisoquinoline)] maleate (1.30 g, 3.7 mmol) was refluxed with 37% formaldehyde (2.8 mL) and 2.0 mL of formic acid for one hour. The solution was cooled, quenched with ice-water (100 mL) and basified with conc. $NH_4OH$. The precipitated oil was partitioned with ether and the dried ether ($MgSO_4$) was concentrated to give an oil (0.9 g). The oil was dissolved in isopropanol (12 mL) and 30% HBr/Acetic acid was added to pH1. After cooling to 0° C., a solid precipitated and was filtered to give the title compound (1.02 g), mp 230°–232.5° C. The salt was purified further by regenerating the free base and reforming the hydrobromide salt in ethanol. The isolated hydrobromide salt was dried at 100° C. in vacuo to give the title product (0.75 g), top. 231°–233° C.

EXAMPLE 4

Resolution of spiro[indane-1,1'-(1',2',3',4'-tetrahydroisoquinoline)]

Spiro[indane-1,1'-(1',2',3',4'-tetrahydroiosquinoline (11.9 g, 0.051 mol) and di-p-toluoyl-D-tartaric acid were each dissolved in 100 mL of hot acetone, filtered and combined. After cooling the solution at 0° C. overnight, the precipitated solids were collected. The solids were slurried with hot acetone and filtered to give the salt which was converted to the free base with 2.5N NaOH. The precipitated base was isolated by extraction into chloroform. The dried chloroform solution ($Na_2SO_4$) was concentrated to yield an oil (5.7 g). The oil (5.7 g) was retreated with di-p-toluoyl-D-tartaric acid (10.2 g) in the same manner as described above to give the salt (12.5 g). The salt (12.5 g) was stirred with 50 mL of water and 50 mL of 2.5N NaOH to liberate the base which was extracted into chloroform, dried and concentrated to give the base (4.7 g). The base was dissolved in hot isopropanol (25 mL), acidified with hydrogen chloride and cooled in a freezer overnight. The precipitated solids were filtered, washed with ether and dried to give (–)-spiro[indane-1,1'-(1',2',3',4'-tetrahydroisoquinoline)]hydrochloride (3.36 g), mp. 274°–278° C., $[\alpha]_D=-33.02°$ (MeOH, 26.8° C.).

The acetone filtrates from above were concentrated and the recovered salt was converted to the free base. A 10.19 g portion of the base and di-p-toluoyl-L-tartaric acid monohydrate (17.3 g) were each dissolved in hot acetone (100 mL) and combined. The solution was stirred at room temperature. The precipitated solids were isolated, restirred with hot acetone and filtered to give the salt. The salt was converted to the free base by treatment with 2.5N NaOH and extraction of the base into chloroform. The dried chloroform solution ($Na_2SO_4$) was concentrated to give the free base (5.5 g). The base was retreated with di-p-toluoyl-L-tartaric acid monohydrate (9.5 g) in hot acetone (100 mL) to give the salt (14 g). The salt was converted to the free base by treatment with 2.5N NaOH (50 mL) and water (50 mL) and the free base was isolated by extraction into chloroform. The isolated base (6.8 g) was dissolved in hot isopropanol and treated with hydrogen chloride. After cooling the solution in a freezer overnight, the precipitated solids were filtered and washed with ether and dried to give (+)-spiro[indane-1,1'-(1',2',3',4'-tetrahydroisoquinoline)]hydrochloride (3 g), mp. 274°– 278° C.,$[\alpha]_D=+26.57°$ (MeOH, 28.6° C.).

What we claim is:

1. A compound of the formula I,

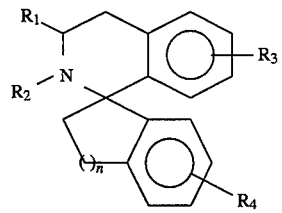

wherein $R_1$ and $R_2$ independently represent H or $C_{1-6}$ alkyl;

$R_3$ and $R_4$ independently represent one to four radicals selected from H, $NH_2$ or chloro;

n is 1 or 2, in addition, the spiro rings may independently contain an unsaturated carbon-carbon bond;

and pharmaceutically acceptable derivatives thereof.

2. A compound according to claim 1 in which $R_1$ and $R_2$ are independently selected from hydrogen, methyl or ethyl.

3. A compound according to claim 1 in which $R_3$ and $R_4$ are hydrogen.

4. A compound according to claim 2 in which $R_1$ is hydrogen or methyl and $R_2$ is hydrogen.

5. A compound according to claim 1 in which n is an integer 1.

6. A compound according to claim 1 which is
spiro[indane-1,1'-(1',2',3',4'-tetrahydroisoquinoline)],
trans-spiro[indane-1,1'-(1',2',3',4'-tetrahydro-3'-methylisoquinoline)],
spiro[indane-1,1'-(1',2',3',4'-tetrahydro-2'-methylisoquinoline)],
(–)-spiro[indane-1,1'-(1',2',3',4'-tetrahydroisoquinoline)], or
(+)-spiro[indane-1,1'-(1',2',3',4'-tetrahydroisoquinoline)],
or a pharmaceutically acceptable derivative thereof.

7. A pharmaceutical composition comprising a compound of formula I, as defined in claim 1, or a pharmaceutically acceptable derivative thereof, in association with a pharmaceutically acceptable adjuvant, diluent or carrier.

8. A process for the preparation of the compounds of formula I, as defined in claim 1, or pharmaceutically acceptable derivatives thereof, which comprises;

preparing a compound of formula I in which $R_2$ is hydrogen by cyclizing the corresponding compound of formula III:

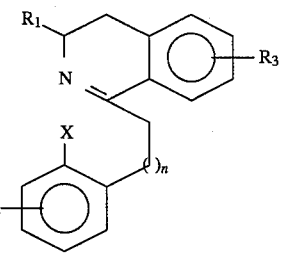

in which $R_1$, $R_3$, $R_4$ and n are as defined above, and X is a suitable leaving group, and where desired or necessary converting the corresponding compound of formula I to a pharmaceutically acceptable derivative thereof or vice-versa.

9. A method for the treatment of neurotoxic injury associated with anoxia, hypoxia or ischemia which comprises administering to a patient a therapeutically effective amount of a compound of formula I, as defined in claim 1, or a pharmaceutically acceptable derivative thereof.

* * * * *